(12) United States Patent
Pellacini et al.

(10) Patent No.: US 6,583,120 B1
(45) Date of Patent: Jun. 24, 2003

(54) ERYTHROMYCIN DERIVATIVE WITH ANTIBIOTIC ACTIVITY

(75) Inventors: Franco Pellacini, Milan (IT); Daniela Botta, Como (IT); Stefano Romagnano, Buccinasco (IT); Enrico Albini, Pavia (IT); Domenico Ungheri, Parabiago (IT); Giovanna Schioppacassi, Milan (IT)

(73) Assignee: Zambon Group S.A., Vicenza (IT)

( * ) Notice: Subject to any disclaimer, the term of this patent is extended or adjusted under 35 U.S.C. 154(b) by 0 days.

(21) Appl. No.: 09/744,245

(22) PCT Filed: Jul. 27, 1999

(86) PCT No.: PCT/EP99/05484

§ 371 (c)(1),
(2), (4) Date: Mar. 2, 2001

(87) PCT Pub. No.: WO00/06586

PCT Pub. Date: Feb. 10, 2000

(30) Foreign Application Priority Data

Jul. 30, 1998 (IT) .......................................... MI98A1775

(51) Int. Cl.[7] .......................... A61K 31/70; C07H 17/08
(52) U.S. Cl. .......................................... 514/29; 536/7.4
(58) Field of Search .............................. 536/7.4; 514/29

(56) References Cited

FOREIGN PATENT DOCUMENTS

WO        WO 96/18633        *  6/1996

* cited by examiner

*Primary Examiner*—Elli Peselev
(74) *Attorney, Agent, or Firm*—Oblon, Spivak, McClelland, Maier & Neustadt, P.C.

(57) ABSTRACT

The present invention discloses an erythromycin derivative with antibiotic activity and pharmaceutically acceptable salts thereof, a process for their preparation and pharmaceutical compositions containing them as active principle.

17 Claims, No Drawings

ERYTHROMYCIN DERIVATIVE WITH ANTIBIOTIC ACTIVITY

This application is a national stage filing under 35 U.S.C. §371 of PCT/EP99/05484, filed Jul. 27, 1999.

The present invention relates to a compound with antibiotic activity, which is useful in the treatment of infectious diseases, and more particularly relates to the compound of formula

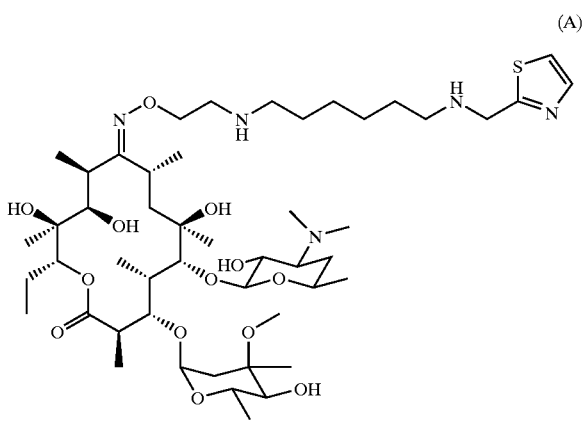

(A)

and to pharmaceutically acceptable salts thereof and pharmaceutical compositions containing it as active principle.

International patent application WO 96/18633 in the name of the Applicant discloses compounds with antibiotic activity, having the following general formula:

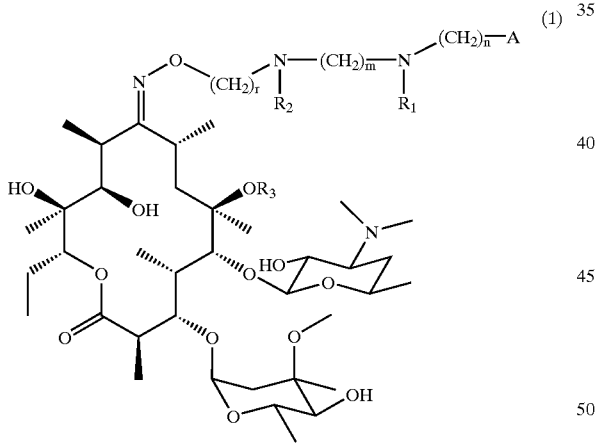

(1)

in which

A is a phenyl or a 5- or 6-membered heterocycle containing one or more hetero atoms chosen from nitrogen, oxygen and sulphur, optionally substituted with 1 to 3 groups, which are the same or different and are chosen from linear or branched $C_1$–$C_4$ alkyl or alkoxy groups, $C_1$–$C_2$ cycloalkene dioxy groups, $C_1$–$C_4$ alkyl sulphonyl groups and phenyl, phenoxy, hydroxyl, carboxyl, nitro, halo and trifluoromethyl groups; $R_1$ and $R_2$ are the same or different hydrogen atom or linear or branched $C_1$–$C_4$ alkyl group; n is 1 or 2; m is an integer from 1 to 8; r is an integer from 2 to 6; $R_3$ is a hydrogen atom or a methyl group.

We have now found that one of the compounds of general formula (I), but not given as an example in the above-mentioned international patent application, has a particularly broad spectrum of activity and a long duration of action, thereby making it extremely useful in antibiotic therapy.

It is an object of the present invention to provide a compound of formula

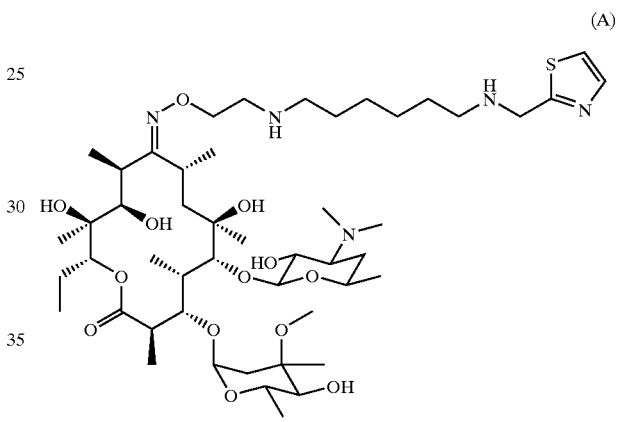

(A)

and pharmaceutically acceptable salts thereof.

Examples of pharmaceutically acceptable salts of compound A are salts with organic or inorganic acids such as hydrochloric acid, hydrobromic acid, hydriodic acid, nitric acid, sulphuric acid, phosphoric acid, acetic acid, tartaric acid, citric acid, benzoic acid, succinic acid and glutaric acid.

The preferred salt is the dihydrochloride.

Compound A of the present invention can be prepared by the synthetic methods already described in patent application WO 96/18633.

In particular, the synthesis of compound A is carried out according to the synthetic scheme given below.

Scheme 1

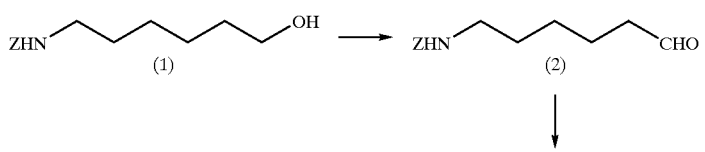

-continued

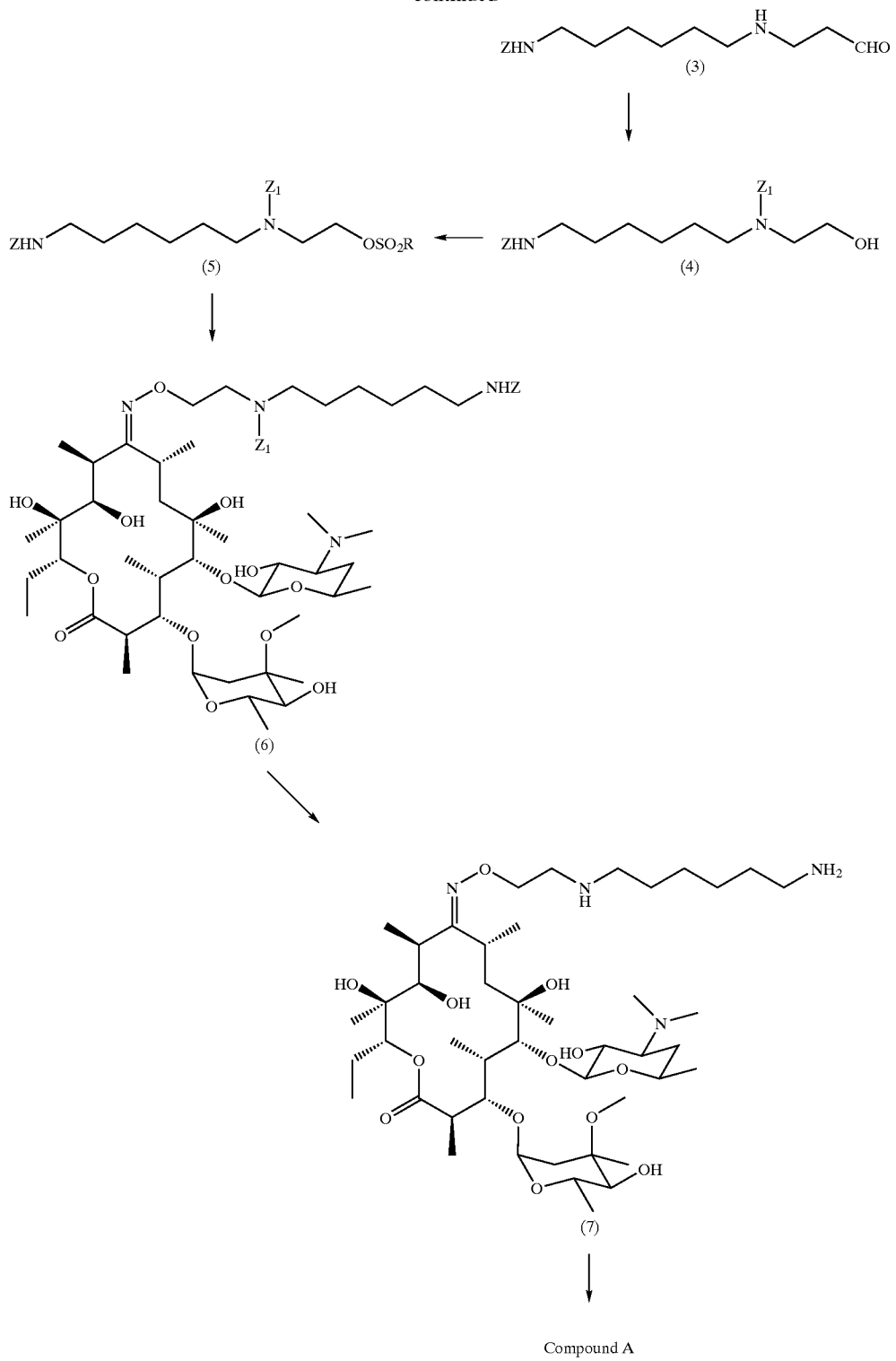

in which
Z and $Z_1$, the same or different, represent a protecting group;
R represents a methyl or p-tolyl group.

The synthesis involves oxidation of the appropriately protected aminohexanol (1) with the corresponding aldehyde by treatment with an oxidizing agent, preferably sodium hypochlorite.

Condensation of the aldehyde (2) with 2-aminoethanol and subsequent reduction of the intermediate imine, preferably with $NaBH_4$, gives the compound (3).

After also protecting the second amino group, the compound (4) is treated with mesyl or tolyl chloride to activate the OH group and allow the subsequent condensation of the activated compound (5) with erythromycin A oxime.

Removal of the protecting groups from the compound (6) gives the amino derivative (7), from which compound A of the present invention is prepared by treatment with the aldehyde of formula

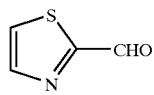

followed by reduction of the intermediate imine.

Compound A of the present invention has a broad spectrum of activity in vitro with respect to Gram-positive and Gram-negative microorganisms (Example 7).

This activity is greater than that of azithromycin on strains of *Streptococcus pneumoniae* and *Streptococcus pyogenes* with erythromycin resistance of inducible type.

However, the property which predominantly differentiates the compound of the present invention from the reference macrolides and also from the compounds of the same class described in the above-mentioned patent application WO 96/18633 is the appreciable duration of action in vivo. Specifically, as reported in Example 8, the therapeutic efficacy of compound A was compared with that of two reference macrolides (clarithromycin and azithromycin) and with that of two compounds described in WO 96/18633 which displayed an excellent activity profile both in vitro and in vivo (compounds 23 and 29 of WO 96/18633).

From the comparison, it is clear that clarithromycin and compound 29 lose most of their efficacy when administered 24 hours before the infection. Compound 23 and azithromycin also lose most of their efficacy 48 and 72 hours, respectively, after administration, while compound A of the present invention is still effective 72 hours after administration.

This particularly prolonged therapeutic efficacy significantly distinguishes compound A from the other reference macrolides, including the structurally related macrolides described in the oft above-mentioned patent application WO 96/18633.

The advantage of prolonged therapeutic efficacy is clear to those skilled in the art, since, from a practical point of view, it allows the dose of antibiotic to be reduced significantly and/or allows the interval between consecutive administrations to be increased, for example going from a prescription plan which involves two dosage intakes per day to a plan which involves only one dosage intake per day.

Compound A can be used in human and veterinary therapy.

For use in therapy, compound A can be used in a pharmaceutical form which is suitable for oral or parenteral administration.

It is therefore a further object of the present invention to provide a pharmaceutical composition containing a therapeutically effective amount of compound A or of a salt thereof, mixed with a pharmaceutically acceptable vehicle.

For the treatment of specific infections, compound A may also be combined with a therapeutically effective amount of another active principle.

The examples below will now be given for the purpose of illustrating the present invention more clearly.

EXAMPLE 1

Preparation of Benzyl [6-(2-Hydroxyethylamino)-hexyl]carbamate

A solution of KBr (1.18 g; 9.94 mmol) in water (20 ml) and TEMPO (0.155 g; 0.994 mmol) were added to a solution, cooled with ice to about 10° C., of benzyl (6-hydroxyhexyl)carbamate (25 g; 99.47 mmol), prepared as described in patent application WO 96/18633, in methylene chloride (350 ml), followed by dropwise addition over about 15–20 minutes, while keeping the temperature at 10–12° C., of a solution prepared with $NaHCO_3$ (7.5 g; 89.28 mmol) and NaOCl (4.5% aqueous solution; 197 ml; 125 mmol).

15 minutes after the end of the dropwise addition, the phases were separated and the aqueous phase was extracted once with methylene chloride (100 ml). The combined organic extracts were washed twice with saline solution (20% NaCl) and dried over sodium sulphate.

3 Å molecular sieves (30 g) were added to the solution obtained (about 800 ml), followed by rapid dropwise addition, while cooling with ice and water, of a solution of 2-aminoethanol (35.9 ml; 0.597 mol) in ethanol (600 ml).

After completion of the dropwise addition, the mixture was stirred at room temperature for 2 hours and filtered.

$NaBH_4$ (4.54 g; 120 mmol) was added portionwise to the solution obtained, stirred under a nitrogen atmosphere and cooled with water and ice.

At the end of the addition, the reaction mixture was stirred at room temperature for 2 hours and the solvent was then evaporated off.

The residue was taken up in water and ethyl acetate, the phases were separated and the aqueous phase was extracted twice more with ethyl acetate.

The combined organic extracts were washed with saline solution (20% NaCl), dried over sodium sulphate and concentrated to give an oily residue which solidified.

The residue was triturated with hexane, filtered off and washed with a mixture of hexane and ethyl ether to give benzyl [6-(2-hydroxyethyl-amino)hexyl]carbamate (26.22 g; 89% yield) as a white solid.

$^1$H-NMR ($CDCl_3$) δ: 7.33–7.25 (m, 5H, Ar); 5.05 (s, 2H, $COOCH_2$); 4.96 (broad t, 1H, NH); 3.63–3.58 (m, 2H, *$CH_2$—OH); 3.19–3.09 (m, 2H, $CH_2NCO$); 2.72–2.67 (m, N—*$CH_2$—$CH_2O$); 2.59–2.52 (m, 4H, OH and $CH_3$); 1.53–1.23 (m, 8H, $4CH_2$).

EXAMPLE 2

Preparation of Benzyl 6-(Benzyloxycarbonylaminohexyl)-(2-hydroxyethyl)carbamate

A solution of benzyl chloroformate (50% in toluene; 42.5 ml; 0.128 mol) in ethyl acetate (85.5 ml) and 1N NaOH (128 ml; 0.128 mol) were simultaneously added dropwise to a solution, cooled to 0–5° C., of benzyl [6-(2-hydroxyethylamino)hexyl]carbamate (31.5 g; 0.107 mol), prepared as described in Example 1, in a mixture of water (87 ml), 1N NaOH (17 ml) and ethyl acetate (180 ml), while controlling the temperature and the pH (to about 8).

After completion of the dropwise addition, the reaction mixture was stirred for 30 minutes at 0–5° C., the cooling bath was then removed and further 1N NaOH (15 ml) was added to bring the pH to 8, after which the mixture was left stirring at room temperature overnight.

The phases were separated and the aqueous phase was extracted again with ethyl acetate. The combined organic extracts were washed with saline solution, dried over sodium sulphate and concentrated under vacuum to give an oily residue.

Chromatographic purification (eluent: from 60/40 to 70/30 ethyl acetate/petroleum ether) gave benzyl 6-(benzyloxycarbonylaminohexyl)(2-hydroxyethyl) carbamate as an oil (42.5 g; 92% yield).

$^1$H-NMR (CDCl$_3$) δ: 7.39–7.25 (m, 10H, Ar); 5.10 and 5.07 (2s, 4H, 2COOCH$_2$); 3.71 (broad signal, 2H, *CH$_2$—OH); 3.43–3.01 (m, 4H, 2CH$_2$NCO); 1.57–1.19 (m, 8H, 4CH$_2$).

EXAMPLE 3

Preparation of 2-[Benzyloxycarbonyl(6-benzyloxycarbonylaminohexyl)amino]ethyl Methanesulphonate Trethylamine (8.95 ml; 64.31 mmol) was added to a solution of benzyl 6-(benzyloxycarbonylaminohexyl)-(2-hydroxyethyl)carbamate (13.78 g; 32.15 mmol), prepared as described in Example 2, in methylene chloride (140 ml). The mixture was cooled to 0–5° C. and a solution of methanesulphonyl chloride (3.36 ml; 43.41 mmol) in methylene chloride (20 ml) was then added dropwise.

After completion of the addition, the reaction mixture was stirred at room temperature for 60 minutes and then washed with 5% aqueous citric acid, with saline solution (20% NaCl), with 5% aqueous NaHCO$_3$ and finally again with saline solution. After drying over sodium sulphate and evaporation under vacuum, 2-[benzyloxycarbonyl(6-benzyloxycarbonylaminohexyl)amino]ethyl methanesulphonate (16.37 g; 100% yield) was obtained as a brown oil.

$^1$H-NMR (CDCl$_3$) δ: 7.35–7.27 (m, 10H, Ar); 5.11 and 5.07 (2s, 4H, 2COOCH$_2$); 4.36–4.19 (m, 2H, CH$_2$OSO$_2$); 3.57–3.51 (m, 2H, SO—CH$_2$—*CH$_2$N): 3.32–3.07 (m, 4H, 2CH$_2$N); 2.91 and 2.85 (2s conformers, 3H, CH$_3$); 1.50–1.20 (m, 8H, 4CH$_2$).

EXAMPLE 4

Preparation of Erythromycin A (E)-9-[O-[2-[Benzyloxycarbonyl(6-benzyloxycarbonylaminohexyl)amino]ethyl]oxime 95% potassium tert-butoxide (4.178 g; 35.37 mmol) was added to anhydrous tetrahydrofuran (165 ml), with stirring under a nitrogen atmosphere. After cooling with water and ice to about 10° C., erythromycin A oxime (24.08 g; 32.15 mmol) was added portionwise.

The reaction mixture was stirred for 30 minutes and 18-crown-6 ether (8.5 g; 32.15 mmol) was added, followed by a solution of 2-[benzyloxycarbonyl(6-benzyloxycarbonylaminohexyl)amino]ethyl methanesulphonate (16.37 g; 32.15 mmol), prepared as described in Example 3, in anhydrous tetrahydrofuran (65 ml), and the mixture was left stirring at room temperature overnight.

After evaporation of the solvent, the residue was taken up in a mixture of ethyl acetate and saline solution (20% NaCl) and the phases were separated. The aqueous phase was extracted again with ethyl acetate. The combined organic extracts, washed twice with saline solution and dried, were concentrated under vacuum to give a foamy solid residue.

Chromatographic purification (eluent: 90/7/0.7 CH$_2$Cl$_2$/CH$_3$OH/NH$_3$) gave erythromycin A (E)-9-[O-[2-[benzyloxycarbonyl(6-benzyloxycarbonylaminohexyl)amino]ethyl]oxime] (27.1 g; 72% yield) as a pale yellow foamy solid.

$^1$H-NMR (CDCl$_3$) δ: 7.35–7.23 (m, 10H, Ar); 5.10 and 5.06 (2s, 4H, 2*COOCH$_2$); 3.29 (s, 3H, OMe); 2.26 (s, 6H, Me—N—Me).

EXAMPLE 5

Preparation of Erythromycin A (E)-9-[O-[2-[(6-Aminohexyl)amino]ethyl]oxime]

10% Pd/C (2.7 g) was added to a solution of erythromycin A (E)-9-[O-[2-[benzyloxycarbonyl(6-benzyloxycarbonylaminohexyl)amino]ethyl]oxime] (27.1 g; 23.37 mmol), prepared as described in Example 4, in ethanol (407 ml). The mixture was hydrogenated in a Parr hydrogenator. Once the consumption of H$_2$ was complete, the catalyst was filtered off and the solution was evaporated to give a white foamy solid residue.

Chromatographic purification (eluent: from 85/15/1.5 to 80/20/2 CH$_2$Cl$_2$/CH$_3$OH/NH$_3$) gave erythromycin A (E)-9-[O-[2-[(6-aminohexyl)amino]ethyl]oxime] (15.4 g; 74% yield) as a white solid.

$^1$H-NMR (CDCl$_3$) δ: 4.22–3.93 (m, 2H, NOCH$_2$); 3.28 (s, 3H, OMe); 2.25 (s, 6H, Me—N—Me).

EXAMPLE 6

Preparation of Erythromycin A (E)-9-[O-[2-[6-[(Thiazol-2-ylmethyl)amino]hexyl]amino]ethyl] oxime] (Compound A)

97% 2-thiazolecarbaldehyde (1 g; 8.57 mmol) and 95% sodium cyanoborohydride (0.9 g; 13.71 mmol) were added, with stirring at room temperature, to a solution of erythromycin A (E)-9-[O-[2-[(6-aminohexyl)amino]ethyl]oxime] (7.64 g; 8.57 mmol), prepared as described in Example 5, in methylene chloride (50 ml), followed by addition of acetic acid to bring the pH to about 6 (2 ml).

After dilution with methylene chloride (10–20 ml), the reaction mixture was stirred overnight at room temperature.

After addition of water acidified to pH 5–6 with acetic acid, the precipitate was filtered off, the phases were separated and the aqueous phase was extracted again with methylene chloride.

The aqueous phase was basified with NaHCO$_3$ to pH 8 and extracted three times with methylene chloride.

The organic extracts were dried and concentrated under vacuum to give a foamy solid residue.

Chromatographic purification (eluent: 90/10/1 CH$_2$Cl$_2$/CH$_3$OH/NH$_3$) gave compound A (2.04 g; 24% yield).

$^1$H-NMR (200 MHz-CDCl$_3$): δ (ppm): 7.66 (d, J=3.4); 7.21 (d, J=3.4); $^{13}$C-NMR (200 MHz-CDCl$_3$): 142.43; 118.72; 171.98; 174.93; 171.84.

EXAMPLE 7

In Vitro Antibacterial Activity

The minimum inhibitory concentrations (MIC), with respect to Gram-positive bacteria (erythromycin-sensitive and -resistant strains) and Gram-negative bacteria, were determined by means of the broth-scalar dilution micromethod in twin series [National Committee for Clinical Laboratory Standards, 1990; Methods for dilution antimicrobial susceptibility tests for bacteria that grow aerobically; Approved standards M7-A2-NCCLS, Villanova, Pa.], using Mueller Hinton Broth (MHB) as culture medium.

In the case of demanding bacteria, the medium was supplemented with 5% horse serum (*Streptococcus pneumoniae* and *Streptococcus pyogenes*) or 5% Fildes enrichment (*Haemophilus influenzae* and *Branhamella catarrhalis*).

Roxithromycin, clarithromycin and azithromycin [The Merck Index, XIIth edition, Nos. 8433, 2400 and 946, respectively] were used as reference macrolides.

The MIC values, expressed in µg/ml, were determined after incubating the microplates at 37° C. for 18 hours, by evaluating the lowest antibiotic concentration capable of inhibiting the bacterial growth.

TABLE 1

In vitro antibacterial activity, expressed as MIC (µg/ml), of compound A and of the reference compound (azithromycin) with respect to recently clinically isolated, erythromycin-resistant strains of *Streptococcus pneumoniae*.

| Streptococcus | MIC (µg/ml) | |
|---|---|---|
| pneumoniae | Compound A | Azithromycin |
| Strain 1035 | 2 | 2 |
| Strain 1047 | 2 | 4 |
| Strain 1051 | 1 | 64 |
| Strain 1188 | 2 | 8 |
| Strain 1392 | 4 | 16 |
| Strain 9114 | 0.25 | 32 |
| Strain 871 | 0.5 | 2 |
| Strain 9117 | 0.25 | 64 |

TABLE 2

In vitro antibacterial activity, expressed as MIC (µg/ml), of compound A and of the reference compounds (azithromycin, clarithromycin and roxithromycin) with respect to erythromycin-sensitive Gram-positive and Gram-negative microorganisms.

| MICRO-ORGANISM (number of strains tested) | COMPOUND | MIC (µg/ml) | | |
|---|---|---|---|---|
| | | 50% | 90% | Range |
| Streptococcus pneumoniae (18) | Compound A | 0.0039 | 0.0156 | 0.0019–0.25 |
| | Azithromycin | 0.0312 | 0.0625 | 0.0156–0.5 |
| | Clarithromycin | 0.0156 | 0.0156 | 0.0039–0.125 |
| | Roxithromycin | 0.0625 | 0.0625 | 0.0156–0.5 |
| Streptococcus group A (15) | Compound A | 0.0156 | 0.0312 | 0.0078–0.5 |
| | Azithromycin | 0.0625 | 0.125 | 0.0625–1 |
| | Clarithromycin | 0.0156 | 0.0156 | 0.0078–0.25 |
| | Roxithromycin | 0.0625 | 0.0625 | 0.0312–1 |
| Streptococcus agalactiae (4) | Compound A | 0.0156 | 0.25 | 0.0078–0.25 |
| | Azithromycin | 0.0625 | 0.25 | 0.0312–0.25 |
| | Clarithromycin | 0.0312 | 0.0625 | 0.0156–0.0625 |
| | Roxithromycin | 0.125 | 0.25 | 0.0625–0.25 |
| Staphylococcus aureus (13) | Compound A | 0.5 | 0.5 | 0.25–1 |
| | Azithromycin | 0.5 | 1 | 0.5–1 |
| | Clarithromycin | 0.25 | 0.25 | 0.125–0.25 |
| | Roxithromycin | 0.5 | 1 | 0.25–1 |
| Haemophilus influenzae (11) | Compound A | 4 | 4 | 1–8 |
| | Azithromycin | 0.5 | 1 | 0.25–1 |
| | Clarithromycin | 4 | 1 | 2–8 |
| | Roxithromycin | 8 | 8 | 4–16 |
| Branhamella catarrhalis (5) | Compound A | 0.125 | 0.125 | 0.0019–0.125 |
| | Azithromycin | 0.0156 | 0.0156 | 0.0078–0.0156 |
| | Clarithromycin | 0.0156 | 0.0156 | 0.0078–0.0156 |
| | Roxithromycin | 0.0312 | 0.0625 | 0.0312–0.0625 |
| Klebsiella pneumoniae (6) | Compound A | 16 | 32 | 16–32 |
| | Azithromycin | 4 | 8 | 4–8 |
| | Clarithromycin | 64 | 64 | 64 |
| | Roxithromycin | >64 | >64 | >64 |
| Escherichia coli (3) | Compound A | | | 1–8 |
| | Azithromycin | | | 2–4 |
| | Clarithromycin | | | 16–64 |
| | Roxithromycin | | | 64–>64 |

The data given in Tables 1 and 2 show that the spectrum of activity of compound A is particularly broad (Gram-positive bacteria, both erythromycin-sensitive and erythromycin-resistant, and Gram-negative bacteria) and that the activity is greater than that of the reference macrolides.

EXAMPLE 8

In Vivo Antibacterial Activity

The therapeutic efficacy, expressed as the 50% protective dose ($PD_{50}$), of compound A was evaluated in the experimental pulmonary infection induced in mice with *Streptococcus pneumoniae* UC 41 and with *Streptococcus pyogenes* C 203.

Charles River albino mice (CD 1 strain) weighing 23–25 g were used, kept in groups of 6 per cage, and were fed normally with a standard diet and water ad libitum.

A microorganism suspension (equal to about $10^8$ CFU) in tryptone broth (0.05 ml) was administered intranasally to each mouse, anaesthetized with a mixture of ethyl ether and chloroform.

Compound A, compound 23 and compound 29 of WO 96/18633 and azithromycin and clarithromycin, used for comparative purposes, were administered orally in a single dose, as a 0.5% suspension in Methocel® 1 hour after the infection and 24, 48 and 72 hours before the infection.

Observation of the death of the mice was continued for 7 days after the infection.

The $PD_{50}$, expressed as µmol/kg, was calculated by means of the probit analysis.

TABLE 3

In vivo therapeutic efficacy of compound A and of the comparative compounds after oral administration, in the case of pulmonitis induced with *Streptococcus pneumoniae* UC 41.

| | $PD_{50}$ (µmol/kg) | |
|---|---|---|
| COMPOUND | 24 hours before the infection | 48 hours before the infection |
| Compound A | 16.39 (11.20–23.99) | 25.90 (17.57–38.19) |
| Azithromycin | 16.45 (10.80–25.06) | 34.13 (23.13–50.32) |

95% confidence limit

TABLE 4

In vivo therapeutic efficacy of compound A and of the comparative compounds after oral administration, in the case of pulmonary infection induced with Streptococcus pyogenes C 203

| COMPOUND | $PD_{50}$ ($\mu$mol/kg) | | | |
|---|---|---|---|---|
| | 1 hour after the infection | 24 hours before the infection | 48 hours before the infection | 72 hours before the infection |
| Compound A | 15.45 (10.17–23.46) | 16.39 (11.20–23.99) | 25.90 (17.57–38.19) | 31.51 (22.06–45.03) |
| Clarithromycin | 7.38 (3.77–14.45) | >85.6 | | |
| Azithromycin | 5.32 (3.57–7.91) | 16.45 (10.80–25.06) | 34.13 (23.13–50.32) | >85.4 |
| Compound 23 | 12 | 38.5 | | |
| Compound 29 | 11.8 | >59 | | |

95% confidence limit

From the data given in Tables 3 and 4 it is seen that compound A of the present invention is still effective 72 hours after administration, in contrast with all the comparative compounds.

What is claimed is:

1. A compound of formula A:

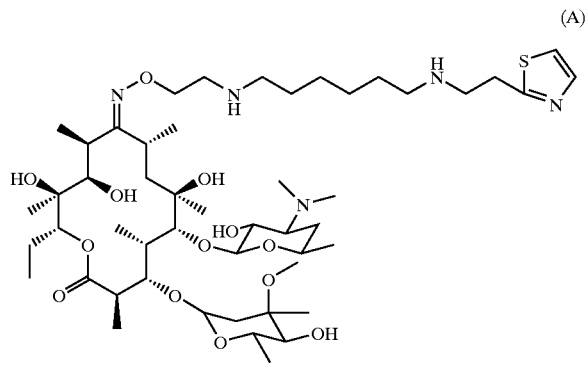

(A)

or a pharmaceutically acceptable salt thereof.

2. A process for preparing Compound A as defined in claim 1 comprising reacting the amino derivative of formula 7:

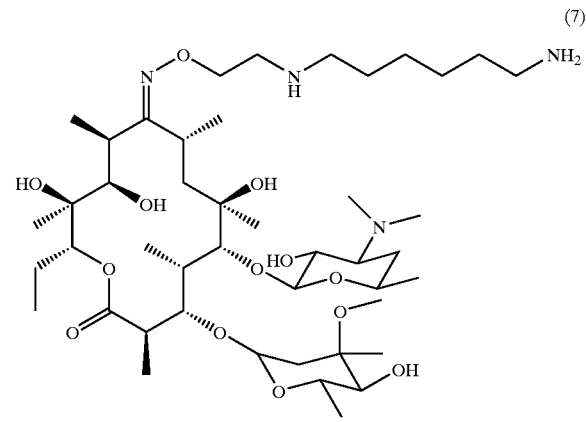

(7)

and the aldehyde of formula:

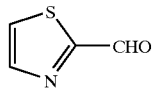

and reducing the intermediate imine.

3. A pharmaceutical composition comprising a therapeutically effective amount of the compound of claim 1 or of a salt thereof, and a pharmaceutically acceptable vehicle.

4. A method for inhibiting bacterial growth comprising contacting a bacterium with an effective amount of the compound of claim 1.

5. The method of claim 4, wherein said bacterium is a gram positive bacterium.

6. The method of claim 4, wherein said bacterium is a gram negative bacterium.

7. The method of claim 4, wherein said bacterium is Staphylococcus.

8. The method of claim 4, wherein said bacterium is Streptococcus.

9. The method of claim 4, wherein said bacterium is Haemophilus.

10. The method of claim 4, wherein said bacterium is Branhamella.

11. The method of claim 4, wherein said bacterium is Klebsiella.

12. The method of claim 4, wherein said bacterium is Escherichia.

13. A method for treating a bacterial infection comprising administering an effective amount of the compound of claim 1 to a subject in need thereof.

14. The method of claim 13, wherein said subject is human.

15. The method of claim 13, wherein said subject is a nonhuman animal.

16. The method of claim 13 comprising oral administration of said compound.

17. The method of claim 13 comprising parenteral administration of said compound.

* * * * *

UNITED STATES PATENT AND TRADEMARK OFFICE
CERTIFICATE OF CORRECTION

PATENT NO.    : 6,583,120 B1
DATED         : June 24, 2003
INVENTOR(S)   : Pellacini et al.

It is certified that error appears in the above-identified patent and that said Letters Patent is hereby corrected as shown below:

<u>Title page,</u>
Item [73], should read -- [73] Assignee: Zambon Group S.p.A., Vicenza (IT) --

Signed and Sealed this

Seventh Day of October, 2003

JAMES E. ROGAN
*Director of the United States Patent and Trademark Office*